(12) United States Patent
McLaughlin et al.

(10) Patent No.: US 10,426,843 B2
(45) Date of Patent: Oct. 1, 2019

(54) DELTA-OPIOID RECEPTOR TARGETED AGENT FOR MOLECULAR IMAGING AND IMMUNOTHERAPY OF CANCER

(71) Applicants: H. LEE MOFFITT CANCER CENTER AND RESEARCH INSTITUTE, INC., Tampa, FL (US); UNIVERSITY OF SOUTH FLORIDA, Tampa, FL (US)

(72) Inventors: Mark L. McLaughlin, Tampa, FL (US); David L. Morse, Tampa, FL (US)

(*) Notice: Subject to any disclaimer, the term of this patent is extended or adjusted under 35 U.S.C. 154(b) by 0 days.

(21) Appl. No.: 16/098,906

(22) PCT Filed: May 4, 2017

(86) PCT No.: PCT/US2017/030962
§ 371 (c)(1),
(2) Date: Nov. 5, 2018

(87) PCT Pub. No.: WO2017/192798
PCT Pub. Date: Nov. 9, 2017

(65) Prior Publication Data
US 2019/0192685 A1 Jun. 27, 2019

Related U.S. Application Data

(60) Provisional application No. 62/331,791, filed on May 4, 2016.

(51) Int. Cl.
*A61K 47/68* (2017.01)
*A61P 35/04* (2006.01)
*A61P 35/00* (2006.01)

(52) U.S. Cl.
CPC ...... *A61K 47/6857* (2017.08); *A61K 47/6849* (2017.08); *A61P 35/00* (2018.01); *A61P 35/04* (2018.01)

(58) Field of Classification Search
None
See application file for complete search history.

(56) References Cited

U.S. PATENT DOCUMENTS

| 4,559,157 | A | 12/1985 | Smith et al. |
| 4,608,392 | A | 8/1986 | Jacquet et al. |
| 4,820,508 | A | 4/1989 | Wortzman et al. |
| 4,938,949 | A | 7/1990 | Borch et al. |
| 4,992,478 | A | 2/1991 | Geria |

(Continued)

FOREIGN PATENT DOCUMENTS

| WO | 2012178063 A1 | 12/2012 |
| WO | 2015200828 A1 | 12/2015 |

OTHER PUBLICATIONS

Huynh et al., Mol Pharm. Feb. 1 2016; 13(2): 534-544 (Year: 2016).*

(Continued)

*Primary Examiner* — Karl J Puttlitz
(74) *Attorney, Agent, or Firm* — Meunier Carlin & Curfman LLC

(57) ABSTRACT

The subject matter disclosed herein relates generally to cancer therapy and to anticancer compounds and imaging agents. More specifically, the subject matter disclosed herein relates to agents that target DOR and their use in the treatment of cancer.

12 Claims, 11 Drawing Sheets

(56) References Cited

U.S. PATENT DOCUMENTS

| | | |
|---|---|---|
| 5,167,649 A | 12/1992 | Zook |
| 6,960,648 B2 | 11/2005 | Bonny |
| 2002/0035243 A1 | 3/2002 | Imfeld et al. |
| 2002/0120100 A1 | 8/2002 | Bonny |
| 2003/0032594 A1 | 2/2003 | Bonny |
| 2006/0104907 A1 | 5/2006 | Lazarus et al. |
| 2011/0097275 A1 | 4/2011 | Arbogast et al. |
| 2017/0202902 A1* | 7/2017 | McLaughlin .......... A61K 38/08 |

OTHER PUBLICATIONS

Balboni et al., J. Med. Chem. 2006, 49, 5610-5617 (Year: 2006).*
Balboni et al. "Synthesis and opioid activity of N,N-dimethyl-Dmt-Tic-NH-CH(R)-R' analogues: acquisition of potent delta antagonism.", Bioorg med Chem 2003, 11:5435-5441.
Keana, "Newer Aspects of Synthesis and Chemistry of Nitroxide Spin Labels", Chemical Reviews, 1978, vol. 78 No. 1, pp. 37-64.
Toyoizumi, et al., "Combined therapy with chemotherapeutic agents and herpes simplex virus type IICP34.5 mutant (HSV-1716) in human non-small cell lung cancer," Human Gene Therapy, 1999, 10(18):17.
Notification of the International Search Report and Written Opinion. Mailed in PCT/US2017/030962 dated Aug. 16, 2017. 14 pages.
Notification of the International Preliminary Report on Patentability. Mailed in PCT/US2017/030962 dated Nov. 15, 2018. 9 pages.
Diaz-Mochon, J. J. et al., "Synthesis and cellular uptake of cell delivering PNA-peptide conjugates", Chemical Communications, 2005, vol. 26, pp. 3316-3318.

* cited by examiner

DELTA-OPIOID RECEPTOR TARGETED AGENT FOR MOLECULAR IMAGING AND IMMUNOTHERAPY OF CANCER

CROSS REFERENCE TO RELATED APPLICATIONS

This application claims the benefit of priority to U.S. Provisional Application 62/331,791, filed May 4, 2016, which is incorporated by reference herein in its entirety.

FIELD

The subject matter disclosed herein relates generally to cancer therapy and to anti-cancer compounds and imaging agents. More specifically, the subject matter disclosed herein relates to agents that target Delta Opioid Receptor (DOR) and their use in the treatment of cancer.

BACKGROUND

Lung cancer is the leading cause of cancer deaths worldwide. Many lung cancer patients are diagnosed with advanced disease. These patients have a low 5-year survival rate and limited treatment options. Thus, novel treatments are needed to improve outcomes for these patients. Recently, immunotherapy agents have been approved for use in lung cancer and many more are being tested in clinical trials. Several of these approved agents are checkpoint inhibitors. By blocking the inhibitory signal, these agents result in an activation of the immune system against the tumor. The current immune checkpoint inhibitor agents are not tumor-targeted. Targeting the immunotherapy agent to specific receptors on tumor cells should concentrate the conjugate in the tumor microenvironment and enhance the immune response in the tumor while reducing the systemic dosages needed, resulting in lower out of tumor toxicity. What are needed are new, targeted agents for immunotherapies and molecular imaging of lung cancer. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds and imaging agents. More specifically, the subject matter disclosed herein relates to agents that target delta-opioid receptor (DOR) and their use in the treatment of cancer. Methods of screening for new agents that target DOR are also disclosed. Also disclosed are PET companion agents and their use with the disclosed compounds.

Additional advantages will be set forth in part in the description that follows or may be learned by practice of the aspects described below. The advantages described below will be realized and attained by elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

In FIG. 3A, expression of the human delta opioid receptor (DOR) mRNA in LKR murine lung cancer cell lines is shows. LKR cells were engineered to express the DOR. The expression of DOR in LKR clones was quantified by qRT-PCR and normalized to the expression of β-actin. LKR clone H1 was selected as the DOR positive cell clone (LKR/DOR). FIG. 3B shows combined results from lanthanide time-resolved fluorescence (LTRF) competitive binding assays. LKR clone H1 (LKR/DOR) cells were incubated with Eu-DPLCE, a europium labeled DOR agonist ($5\times10^{-9}$ M) and increasing concentrations of naloxone, a universal opioid receptor antagonist ($4.88\times10^{-10}$ to $1\times10^{-6}$ M). Naloxone competes with Eu-DPLCE for binding to the delta opioid receptor on LKR clone H1 (LKR/DOR) cells. This results in lower signals at higher concentrations of naloxone. FIG. 3C shows expression of the human DOR protein in LKR parental and LKR clone H1 (LKR/DOR) cells. Representative fluorescence images from confocal microscopy acquisitions. LKR parental cells and LKR clone H1 (LKR/DOR) cells were incubated with DORL-Cy5 ($5\times10^{-8}$ M). Shown in light grey is the signal from DORL-Cy5 and shown in darker grey is signal from DAPI nuclear stain. The parental LKR cells do not express the DOR. LKR clone H1 (LKR/DOR) cells show cell-surface expression of the DOR.

FIG. 4A shows expression of the mouse delta opioid receptor (DOR) mRNA in 344 murine lung cancer cell lines. 344 cells were engineered to express the DOR. The expression of DOR in 344 clones and the 344 parental cell line was quantified by qRT-PCR and normalized to the expression of β-actin. The parental 344 cells do not express the DOR. 344 clone M8 was selected as the DOR positive cell clone (344/DOR). FIG. 4B shows combined results from lanthanide time-resolved fluorescence (LTRF) competitive binding assays. 344 clone M8 (344/DOR) cells were incubated with Eu-DPLCE, a europium labeled DOR agonist ($5\times10^{-9}$ M) and increasing concentrations of naloxone, a universal opioid receptor antagonist ($4.88\times10^{-10}$ to $1\times10^{-6}$ M). Naloxone competes with Eu-DPLCE for binding to the delta opioid receptor on 344 clone M8 (344/DOR) cells. This results in lower signals at higher concentrations of naloxone. FIG. 4C shows expression of the mouse DOR protein in 344 parental and 344 clone M8 (344/DOR) cells. Representative fluorescence images from confocal microscopy acquisitions. 344 parental cells and 344 clone M8 (344/DOR) cells were incubated with DORL-Cy5 ($5\times10^{-8}$ M). Shown in light grey is the signal from DORL-Cy5 and shown in darker grey is signal from DAPI nuclear stain. The parental 344 cells do not express the DOR. 344 clone M8 (344/DOR) cells show cell-surface expression of the DOR.

DETAILED DESCRIPTION

Figure 1:
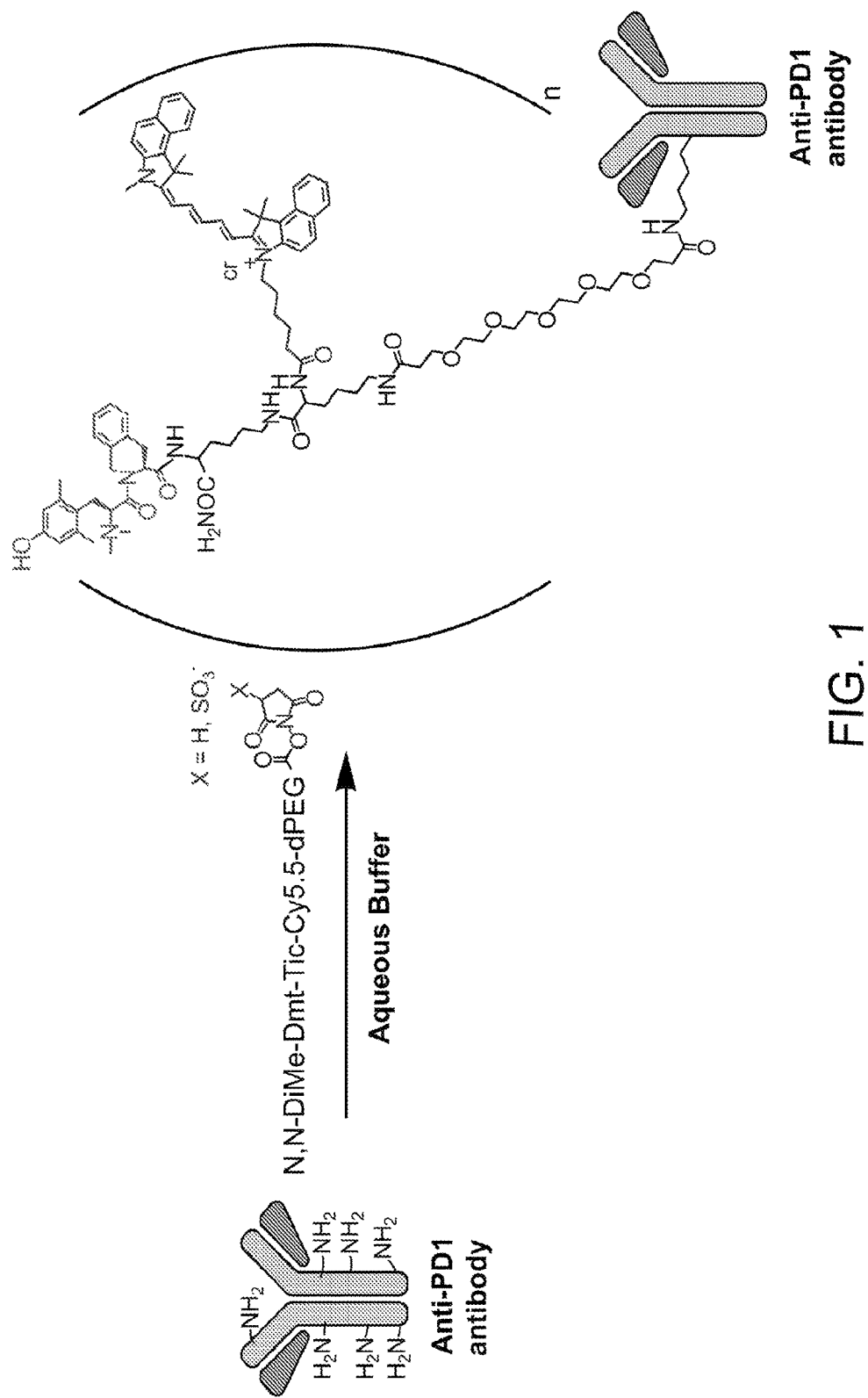
FIG. 1 is a schematic that shows the synthesis of a compound as disclosed herein. Specifically, N,N-Dimethyl-Dmt-Tic-Lys-Lys-Cy5.5-dPEG5 was activated as an N-hydroxysuccinimide (NHS) ester or a sulfo-NHS ester and reacted with the free lysines on the anti-PD1 antibody. Antibodies with targeting ligand-to-antibody ratios (n) of 4.1 (DORL4-PD1), 9.3 (DORL9-PD1) and 12.89 (DORL12-PD1) were used in these studies.
Figure 2A:
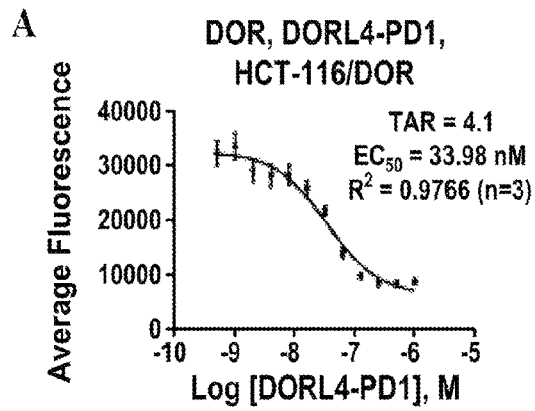
FIGS. 2A-2C show data from combined results from lanthanide time-resolved fluorescence (LTRF) competitive binding assays with DORL-PD1 that have varying targeting ligand-to-antibody ratios (TARs). Results are shown for DORL4-PD1 with a TAR of 4.1 (FIG. 2A), DORL9-PD1 with a TAR of 9.3 (FIG. 2B), and DORL12-PD1 with a TAR of 12.89 (FIG. 2C). HCT-116/DOR cells were incubated with Eu-DPLCE, a europium labeled DOR agonist ($5\times10^{-9}$ M) and increasing concentrations of each DORL-PD1 ($4.88\times10^{-10}$ to $1\times10^{-6}$ M for DORL4-PD1 (FIG. 2A), $9.77\times10^{-10}$ to $2.5\times10^{-7}$ M for DORL9-PD1 (FIG. 2B), and $6.10\times10^{-11}$ to $1\times10^{-6}$ M for DORL12-PD1 (FIG. 2C)). DORL-PD1 competes with Eu-DPLCE for binding to the delta opioid receptor on HCT-116/DOR cells. This results in lower signals at higher concentrations of DORL-PD1 Immunoconjugates with higher TAR bind with higher affinity to the DOR.
Figure 2B:
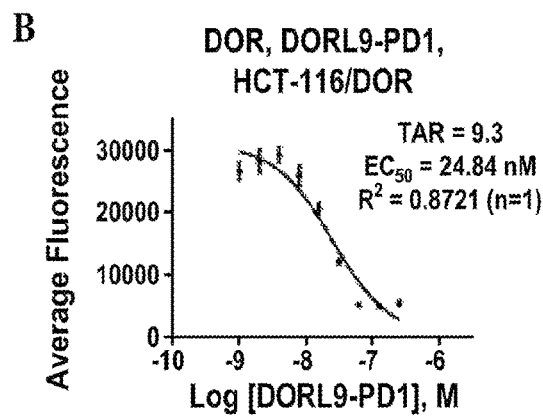
Figure 2C:
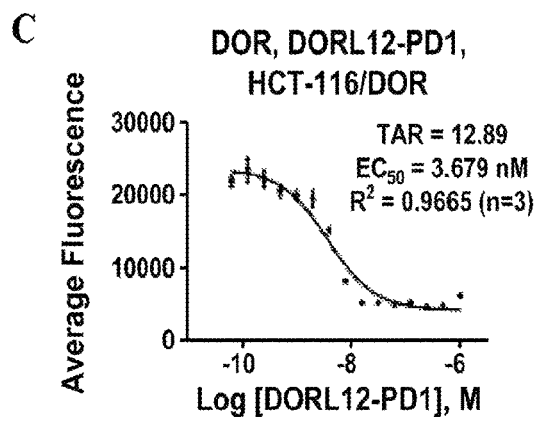
Figures 3A, 3B, 3C:
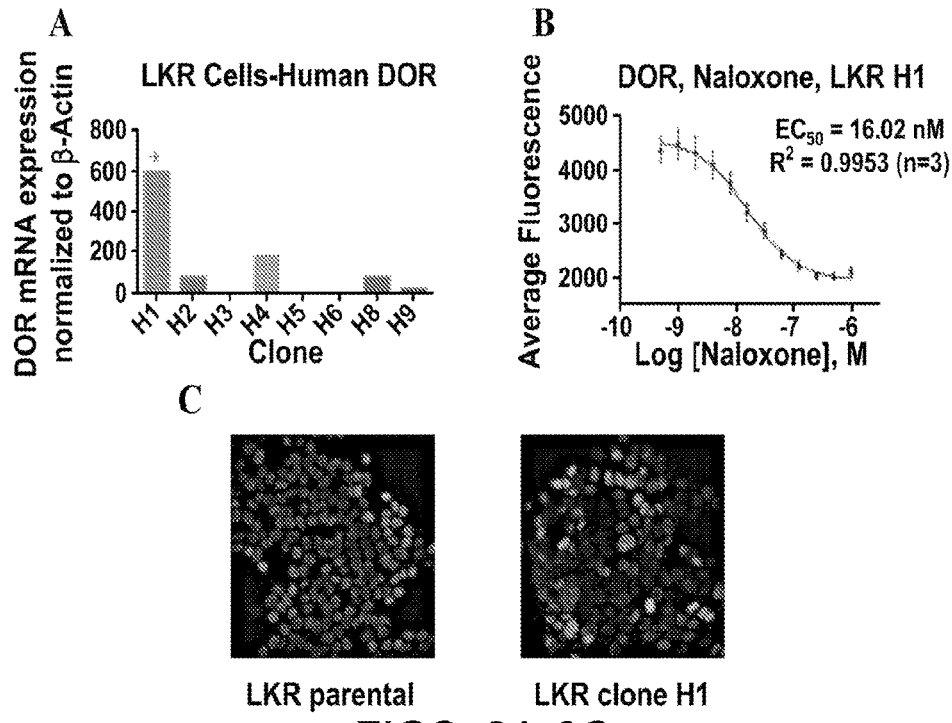
FIGS. 3A-3C show data from screening engineered LKR murine lung cancer cell clones for DOR expression.
Figures 4A, 4B, 4C:
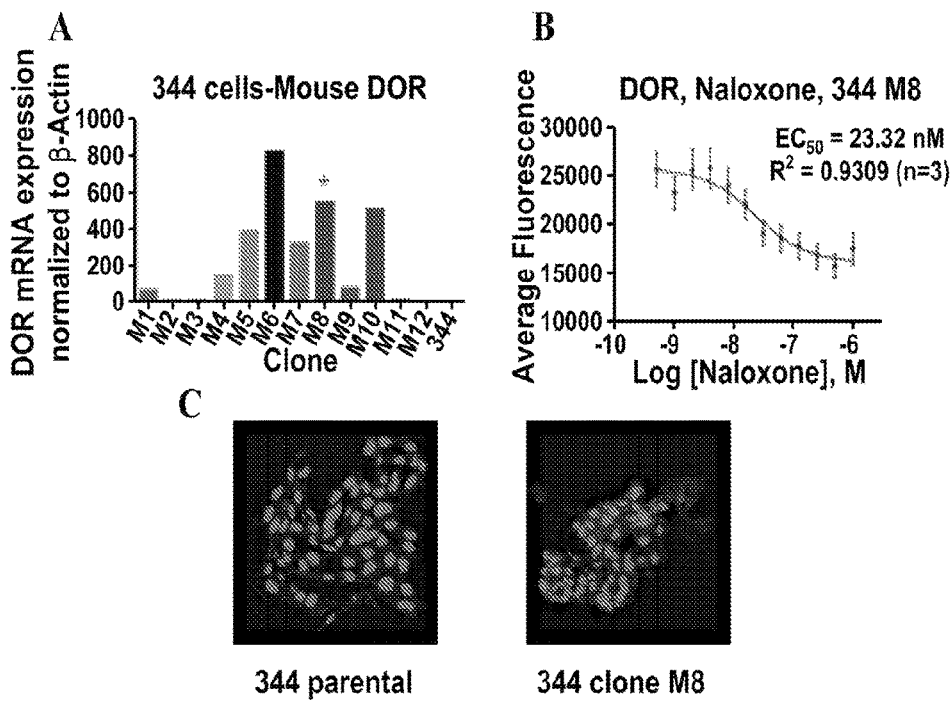
FIGS. 4A-4C contain data from screening engineered 344 murine lung cancer cell clones for DOR expression.
Figure 5:
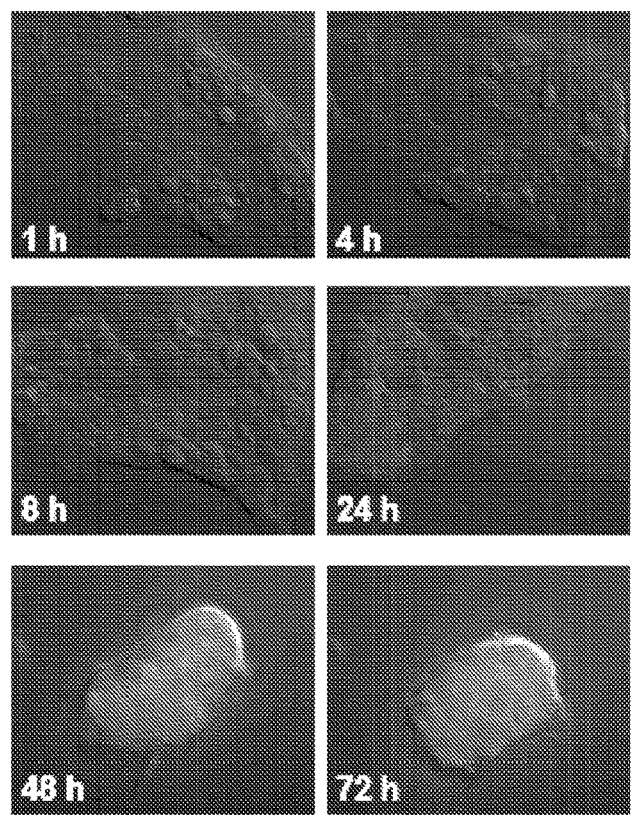
FIG. 5 contains data from in vitro live cell labeling of 344/DOR tumor cells with DIRL-4-PD1. 344/DOR cells were incubated with 150 nM DORL4-PD1 for 30 minutes and then rinsed. Shown are representative live cell fluorescence images of the same region of cells acquired at select time points from 1 hour to 72 hours post-administration of DORL4-PD1.
Figure 6:
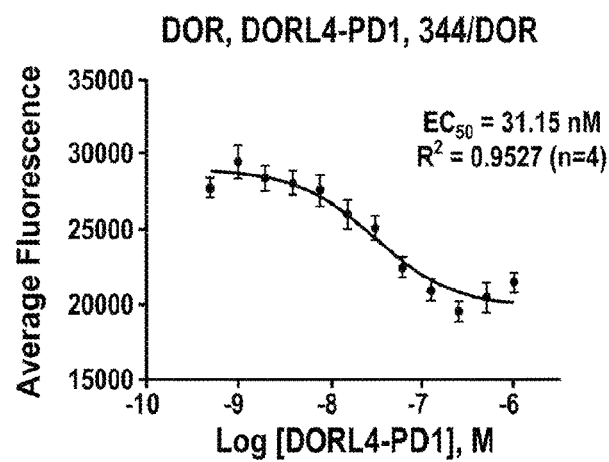
FIG. 6 contains data from in vitro competitive binding assays with DORL4-PD1 on 344/DOR engineered murine lung cancer cells. Combined results from lanthanide time-resolved fluorescence (LTRF) competitive binding assays. 344/DOR cells were incubated with Eu-DPLCE, a europium labeled DOR agonist ($5\times10^{-9}$ M) and increasing concentrations of DORL4-PD1 ($4.88\times10^{-10}$ to $1\times10^{-6}$ M). DORL4-PD1 competes with Eu-DPLCE for binding to the delta opioid receptor on 344/DOR cells. This results in lower signals at higher concentrations of DORL4-PD1.

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Compounds

The delta opioid receptor (DOR) has been reported to be overexpressed in some lung cancers and not in normal lung. Expression of the DOR in lung cancer patient samples by immunohistochemical staining of a tissue microarray has been validated. In addition, the synthesis of fluorescently-labeled DOR-targeted imaging agents (DORL-Cy5 and DORL-800) based on a synthetic peptide antagonist (Dmt-Tic) have been previously reported. These agents have high DOR binding affinity in vitro, demonstrate selectivity for the DOR in vitro and in vivo, and exhibit good pharmacokinetic and biodistribution profiles in vivo. Thus, it has been decided to develop lung cancer-specific immunotherapy agents targeting the DOR by conjugating DORL to immunomodulatory molecules. Disclosed herein a fluorescently-labeled DOR targeting ligand (N,N-Dimethyl-Dmt-Tic-Lys-Lys-Cy5.5-dPEG5) was synthesized and conjugated to an anti-PD1 antibody as the immunomodulatory molecule (DORL-PD1). Immunoconjugates were synthesized with several targeting ligand-to-antibody ratios (TAR). These immunoconjugates were evaluated for differences in binding affinity using lanthanide time-resolved fluorescence (LTRF) competitive binding assays. 344 and LKR murine lung cancer cells were engineered to constitutively express the DOR. Clones of the lung cancer cell lines were screened for expression of the DOR gene using qRT-PCR. Expression of DOR protein was analyzed using confocal microscopy and LTRF competitive binding assays. The binding affinity of DORL4-PD1 was evaluated in the 344/DOR cells using LTRF competitive binding assays. The binding and uptake of DORL4-PD1 in vitro was characterized using live-cell fluorescence microscopy.

In specific aspects, disclosed are compounds having Formula I.

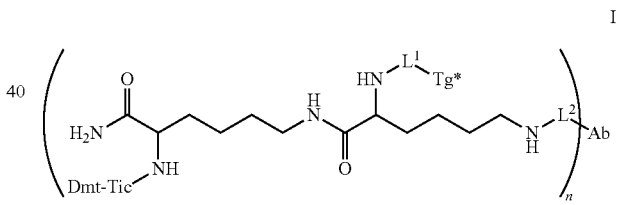

wherein
n is an integer of from 1 to 50;
$L^1$ and $L^2$ are optional linking moieties of from 1 to 100 atoms in length; and
Ab is an antibody, e.g., an antibody specific for programed cell death protein 1 (PD1);
Tg* is H, a protecting group, or a detectable moiety; and
Dmt-Tic is represented by

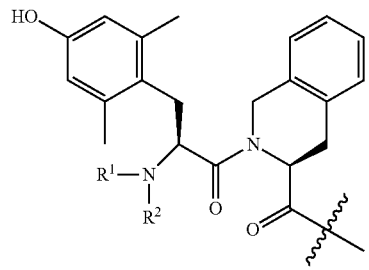

where $R^1$ and $R^2$ are independently selected from H and $CH_3$.

Specific examples of the Dmt-Tic moiety can be found in Balboni et al. Biorg Med Chem 2003, 11:5435-5441, which is incorporated by referenced herein in its entirety for examples of Dmt-Tic moieties.

Compounds of Formula I can be protected or unprotected. Examples of protecting groups are tritly, Fmoc, Boc, benzyl, acetate, 4-phenylbutyryl, Ac-homophenylalanine, and the like.

The compounds described can contain herein contain a linker ($L^1$ and $L^2$) that connects the Tg* and antibody moieties to the lysine residues. Either $L^1$ or $L^2$ can be absent from the compounds disclosed herein (that is $L^1$ or $L^2$ can be null). The term "linker", as used herein, refers to one or more polyfunctional, e.g., bi-functional or tri-functional molecules. The linker can be a single atom, such as a heteroatom (e.g., O, N, or S), a group of atoms, such as a functional group (e.g., amine, —C(=O)—, —CH$_2$—), or multiple groups of atoms, such as an alkylene chain or alkoxyl chain. Suitable linkers include but are not limited to oxygen, sulfur, carbon, nitrogen, alkyl, alkenyl, cycloalkyl, cycloalkenyl, heterocycloalkyl, alkoxyl, aryl, heteroaryl, ether, amine, diamine, amide, alkylamine, thioether, carboxylates, polyethylene, polypropylene, derivatives or combinations thereof.

The linker can be $R^{14}$, C(O)$R^{14}$C(O), C(O)O$R^{14}$OC(O), C(O)$R^{14}$N, C(O)O$R^{14}$NH, NH$R^{14}$NH, or C(O)NH$R^{14}$NHC(O), C(S)O$R^{14}$OC(S); wherein $R^{14}$ is O, S, $C_1$-$C_{20}$ alkyl; $C_1$-$C_{20}$ heteroalkyl; $C_1$-$C_{20}$ alkylamine; $C_1$-$C_{20}$ alkoxyl; $C_1$-$C_{20}$ alkanoyloxyl; or $C_1$-$C_{20}$ alkylamido, any of which can be optionally substituted with one or more substituents including halogen, alkoxyl, alkyl, alkenyl, cycloalkyl, cycloalkenyl, heterocycloalkyl, aryl, heteroaryl, amine, cyano, nitro, hydroxyl, carbonyl, acyl, carboxylic acid (—COOH), —C(O)$R^{12}$, —C(O)O$R^{12}$, carboxylate (—COO$^-$), primary amide (e.g., —CONH$_2$), secondary amide (e.g., —CONH$R^{12}$), —C(O)N$R^{12}R^{13}$, —N$R^{12}R^{13}$, —N$R^{12}$S(O)$_2R^{13}$, —N$R^{12}$C(O)$R^{13}$, —S(O)$_2R^{12}$, —S$R^{12}$, and —S(O)$_2$N$R^{12}R^{13}$, sulfinyl group (e.g., —SO$R^{12}$), and sulfonyl group (e.g., —SOO$R^{12}$); wherein $R^{12}$ and $R^{13}$ can each independently be hydrogen, halogen, hydroxyl, alkyl, haloalkyl, alkenyl, alkynyl, cycloalkyl, heterocycloalkyl, aryl, heteroaryl, carbonyl, cyano, amino, alkylamino, dialkylamino, alkoxyl, aryloxyl, cycloalkyl, alkoxycarbonyl, aminocarbonyl, alkylaminocarbonyl, or dialkylaminocarbonyl.

In some embodiments, the linker is N$R^{14}R^{15}R^{16}$ or (CH)$R^{14}R^{15}R^{16}$; wherein the MC1R binding moiety or detectable moiety are bonded to at least one of $R^{14}R^{15}R^{16}$, and wherein $R^{14}$, $R^{15}$, and $R^{16}$ are each independently hydrogen, $C_1$-$C_{20}$ alkyl; $C_1$-$C_{20}$ heteroalkyl; $C_1$-$C_{20}$ alkylamine; $C_1$-$C_{20}$ alkoxy; $C_1$-$C_{20}$ alkanoyloxy; or $C_1$-$C_{20}$ alkylamido; any of which can be optionally substituted with one or more substituents independently selected from the group consisting of halogen; hydroxyl; cyano; nitro; amino; alkylamino; dialkylamino; amido; alkylamido; =O; —S(O)$_2$; —SO—; —S—; —S(O)$_2$N—; haloalkyl; hydroxyalkyl; carboxy; alkoxy; aryloxy; alkoxycarbonyl; aminocarbonyl; alkylaminocarbonyl; and dialkylaminocarbonyl. For example, the linker is —C(O)$R^{14}$)$_3$N, —($R^{14}$)$_3$N, —(S(O)$_2R^{14}$)$_3$N, —(C(O)$R^{14}$)$_3$CH, —($R^{14}$)$_3$CH, or —(S(O)$_2R^{14}$)$_3$CH. In some embodiment, $C_{1-20}$ refers to alkyl groups containing 1, 2, 3, 4, 5, 6, 7, 8, 9, 10, 11, 12, 13, 14, 15, 16, 17, 18, 19, or 20 carbons. In some embodiments, the linker is —(CO—$R^{14}$)$_2$NH, —($R^{14}$)$_2$NH, —(SO$_2R^{14}$)$_2$NH, —(SO$R^{14}$)$_2$NH, —(O$R^{14}$)$_2$NH, —(O—CO—$R^{14}$)$_2$NH, $R^{14}$)$_2$NH, —(CO—$R^{14}$)$_2$CH$_2$, —($R^{14}$)$_2$CH$_2$, —(SO$_2R^{14}$)$_2$CH$_2$, —(SO$R^{14}$)$_2$CH$_2$, —(O—CO—$R^{14}$)$_2$CH$_2$, or —(O$R^{14}$)$_2$CH$_2$. Suitable examples of linkers are C(O)NH(CH$_2$)$_n$—, where n is from 1 to 20, or C(O)(CH$_2$O)$_n$, where n is from 1 to 10.

The Ab moiety is an antibody or fragment thereof that specifically binds to programmed cell death protein 1. PD-1 antibodies are commercially available for human, rabbit, or murine PD-1. Other antibodies can be used in other embodiments, such as PD-L1 antagonist or CD137, OX40, and CD40 agonistic antibodies.

The Tg* moiety can be a detectable moiety. Examples of suitable detectable moieties include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof.

The detectable moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru (dpp)$_3$); Ru (II) tris (1,10-phenanthroline) (Ru(phen)$_3$), tris(2,2'-bipyridine)ruthenium (II) chloride hexahydrate (Ru(bpy)$_3$); erythrosine B; fluorescein; eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitrophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorescein; carboxynaphtofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; and dioctadecylcycloxacarbocyanine; derivatives or combinations thereof.

The detectable moiety can contain a radiolabel, also referred to herein as radioisotope. The radiolabel can also be a therapeutic moiety, i.e., a radiolabel comprising a therapeutic radionuclide such as, $^{90}$Y or $^{177}$Lu. Other examples of suitable radiolabels include, but are not limited to, metal $^{18}$F, $^{64}$Cu, $^{67}$Cu, $^{89}$Zr, $^{111}$In, $^{124}$I, $^{123}$I, and $^{99m}$Tc. In some embodiments, the radiolabel can be chelated by a macrocyclic molecule. Examples of such macrocyclic molecules include, but are not limited to, 2,2',2''-(10-(2-((2,5-dioxopyrrolidin-1-yl)oxy)-2-oxoethyl)-1,4,7,10-tetraazacyclododecane-1,4,7-triyl)triacetic acid (DOTA)-based chelators, diethylene triamine pentaacetic acid (DTPA)-based chelators, and a derivative or a combination thereof.

The detectable moiety can contain a magnetic spin resonance label. Examples of suitable spin resonance label include free radicals such as nitroxide-stable free radicals. Stable free radicals of nitroxides are known in the art, see for example Keana, "Newer Aspects of Synthesis and Chemistry of Nitroxide Spin Labels", Chemical Reviews, 1978, Vol. 78 No. 1, pp. 37-64, which disclosure is incorporated herein by reference. Suitable nitroxides include, but are not limited to, those derived from 2,2,6,6-tetramethylpiperidine-N-oxyl (TEMPO), 2,2,5,5-tetramethylpyrroline-N-oxyl, and 4,4-dimethyloxazolidine-N-oxyl which is a doxyl nitroxide. All of these compounds are paramagnetic and hence capable of excitation or changes in magnetic resonance energy levels and therefore provide imaging. Other nitroxides include, but are not limited to, doxyl nitroxides, proxyl nitroxides, azethoxyl nitroxides, imidazoline derived nitroxides, tetrahydrooxazine derived nitroxides, and the recently synthesized steroid nitroxides, and the like.

Spin labeling, as used herein, is understood to mean "spin label" as that is defined in the Keana article, namely when a nitroxide bearing molecule that is covalently attached to another molecule of interest, the nitroxide grouping does not significantly disturb the behavior of the system under study. Thus, the nitroxide molecule being paramagnetic, simply enhances the energy or excitation level subjected to the magnetic field during the magnetic resonance.

In specific examples, disclosed herein are compounds of Formula I, wherein n is 4, 9 or 12. That is the ratio of DOR ligand with detectably moiety to antibody Ab is 4 to 1. In other examples, n is 5, 6, 7, 8, 9, 10, 11, 12, 13, 14, 15, 16, 17, 18, 19, or 20, where any of the specified values can form an upper or lower endpoint of a range.

In specific examples, disclosed are fluorescent delta opioid receptor (DOR)-targeted immunotherapy agents with different targeting ligands-to antibody ratios (TARs), DORL4-PD1 (TAR=4.1), DORL9-PD1 (TAR=9.3), and DORL12-PD1 (TAR=12.89). These agents have high affinity for the DOR in vitro with higher TARs resulting in higher binding affinity. Two murine lung cancer cell lines (344 and LKR) were engineered to express the DOR. Binding and live cell labeling of one of these engineered cell lines (344/DOR) using DORL4-PD1 is demonstrated. Future studies will evaluate DORL-PD1 in vivo in immunocompetent mice. These agents could be useful for molecular imaging and immunotherapy of lung cancer. In a specific example, the compounds disclosed herein can have the following formula

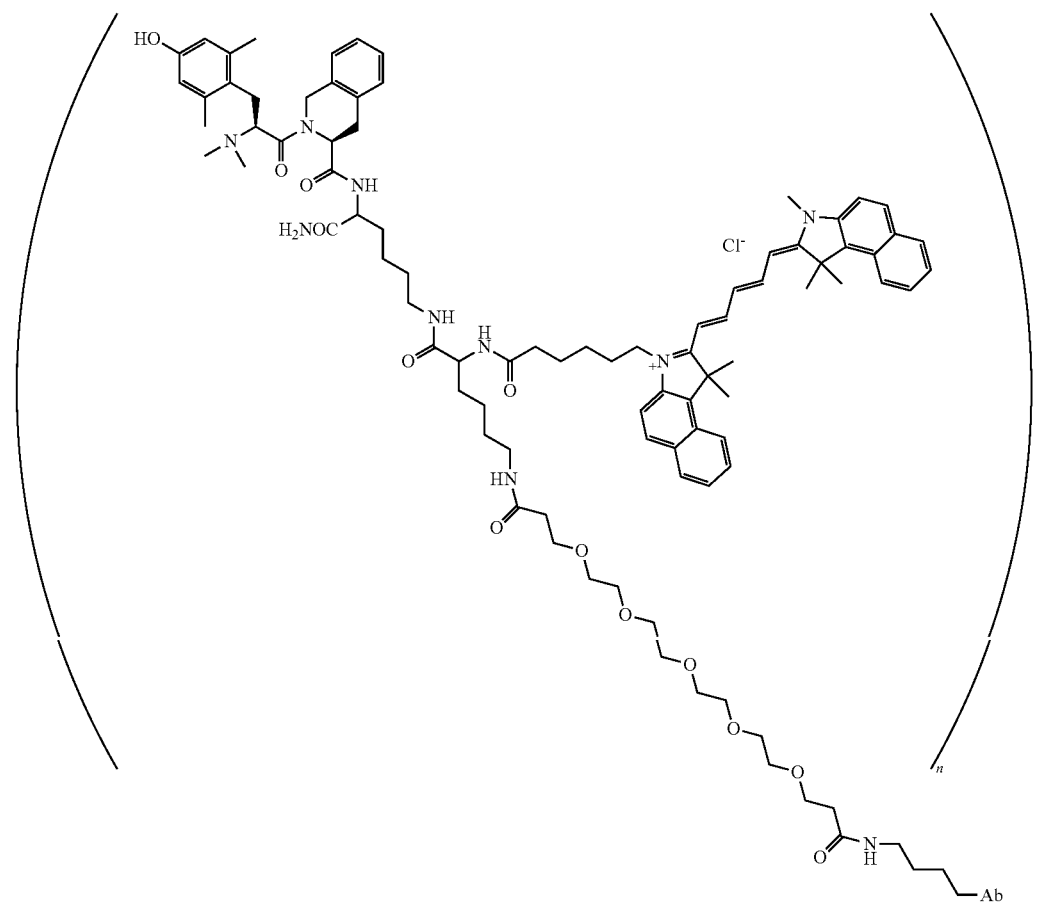

wherein Ab is an antibody as defined herein and n is an integer as defined herein. In a specific example, Ab is PD1.

Also disclosed herein are antibodies conjugated to one or more moieties, which can be the same or different, having the formula

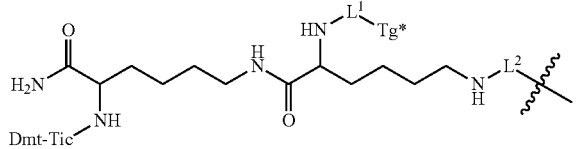

wherein
$L^1$ and $L^2$ are optional linking moieties of from 1 to 100 atoms in length; and
Tg* is H, a protecting group, or a detectable moiety; and
Dmt-Tic is represented by

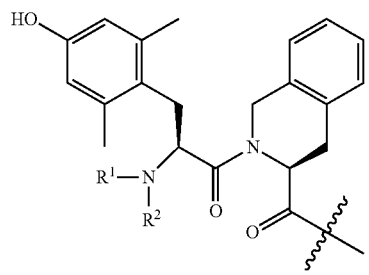

where $R^1$ and $R^2$ are independently selected from H and $CH_3$. The antibodies can be any of the antibodies disclosed herein, e.g., antibodies specific for programed cell death protein 1 (PD1), PD-L1 antagonists, or CD137, OX40, or CD40 agonist antibodies.

Method

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. The compounds disclosed herein are particularly suited for patients with lung cancer. However, other oncological disorders that are characterized by expression of DOR can be treated. Specific examples of such oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In specific examples, the cancer is non-small cell or small cell lung cancer, which are known to overexpress DOR.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

A cancer immunotherapeutic agent suitable for use in the methods disclosed herein is an immunotherapeutic agent which comprises a cell effector component joined to a tumor associated antigen targeting component. Suitable cell effector components can include cytotoxic chemicals, cytotoxic radioisotopes, and cell signaling agents such as cytokines. Suitable tumor targeting components are polypeptide chains which bind to tumor associated antigens present on or in the surrounding tissue matrix of a tumor cell such as receptor protein chains or immunoglobulin chains.

Tumor associated antigens which can be used for targets of the immunotherapeutic agents include a tumor associated antigen selected from the group consisting of AFP, CA 125, CEA, CD19, CD20, CD44, CD45, EGF Receptor, GD[2], GD[3], GM1, GM2, Her-2/Neu, Ep-CAM (KSA), IL-2 receptor, Lewis-Y, Lewis-X (CD 15), melanoma-associated proteoglycan MCSP, PSA and Transferrin Receptor.

Examples of immunotherapeutic agents have an effector component that is a cytokine polypeptide joined to a targeting component which is an immunoglobulin (Ig) polypeptide chain. The Ig polypeptide chain comprises a variable region which binds to a tumor associated antigen. It is preferred that said immunoglobulin chain, when combined with the appropriate complementary chain (i.e. a heavy chain complements a light chain) defines an antibody active site which is specific for a tumor associated antigen.

The tumor targeting Ig portion of the immunotherapeutic agent can comprise an entire immunoglobulin chain amino acid sequence, or at least the fragment of which comprises the antigen binding specificity portion of the protein. Thus, a suitable Ig polypeptide chain will have at least an Ig variable region specific for a tumor associated antigen.

An antibody and polypeptide chains therefrom, suitable for use in the disclosed methods, will have an amino acid sequence that can be of any mammalian origin. Where such antibody protein is not of the same origin as the anticipated patient, fragments of the antibody protein, such as F(ab')2, Fab, Fv or engineered Fv single chain antibody protein can be used. To further reduce antigenicity of the antibody protein, modification of the antibody amino acid sequence may be accomplished to reduce such by making the protein appear more like the patients normal antibody components. For example, monoclonal murine antibody amino acid sequences can be modified to appear more human, for administration to human patients by a variety of processes for humanization of the antibody.

Specific examples of cancer immunotherapeutic agents include an antibody that specifically binds CLTA-4, such as ipilimumab (Bristol-Myers Squibb), anti-PD-1, anti-PDLE Other immunotherapeutic agents include the TNFα antagonists (e.g. etanercept), the B cell depleting agent rituximab, the anti-IL-6 receptor tocilizumab, and the costimulation blocker abatacept can be administered with the compounds or compositions disclosed herein.

The disclosed compounds can also be administered with toll like receptor (TLR) agonist. TLR agonist is a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

The disclosed compounds can also be administered with an angiogenesis inhibiting agent, which is one which can inhibit the formation of new blood vessels (neovascularization) or enlargement of existing capillary networks into the tissues near a tumor cell. Suitable angiogenesis inhibiting agents can be peptides with angiogenesis inhibiting activity, such as the tumor associated antigen PSA. Other suitable angiogenesis inhibiting agents can be antagonists of VEGF associated angiogenesis, for example antagonists of the VEGF receptor on the surface of cells. One monoclonal antibody which can be used is LM609 (ATCC HB 9537).

Administration

The disclosed compounds can be administered either sequentially or simultaneously in separate or combined pharmaceutical formulations. When one or more of the disclosed compounds is used in combination with a second therapeutic agent, the dose of each compound can be either the same as or differ from that when the compound is used alone. Appropriate doses will be readily appreciated by those skilled in the art.

The term "administration" and variants thereof (e.g., "administering" a compound) in reference to a compound as described herein means introducing the compound or a prodrug of the compound into the system of the animal in need of treatment. When a compound as described herein or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," Human Gene Therapy, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation; East Hanover, N.J.) and HERCEPTIN (Genentech, Inc.; South San Francisco, Calif.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEP- TIN). Cytotoxic agents include, for example, radioactive isotopes (e.g., I131, I125, Y90, P32, etc.), and toxins of bacterial, fungal, plant, or animal origin (e.g., ricin, botulinum toxin, anthrax toxin, aflatoxin, jellyfish venoms (e.g., box jellyfish, etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods described herein are further provided. By "kit" is intended any manufacture (e.g., a package or a container) comprising at least one reagent, e.g., anyone of the compounds described herein. The kit can be promoted, distributed, or sold as a unit for performing the methods described herein. Additionally, the kits can contain a package insert describing the kit and methods for its use. Any or all of the kit reagents can be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

The methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Conjugate Synthesis:

PD-1 antibody (Ab) was treated with an activated N,N-DiMe-Dmt-Tic-Cy5.5-dPEG in aqueous buffer as shown in Scheme 1.

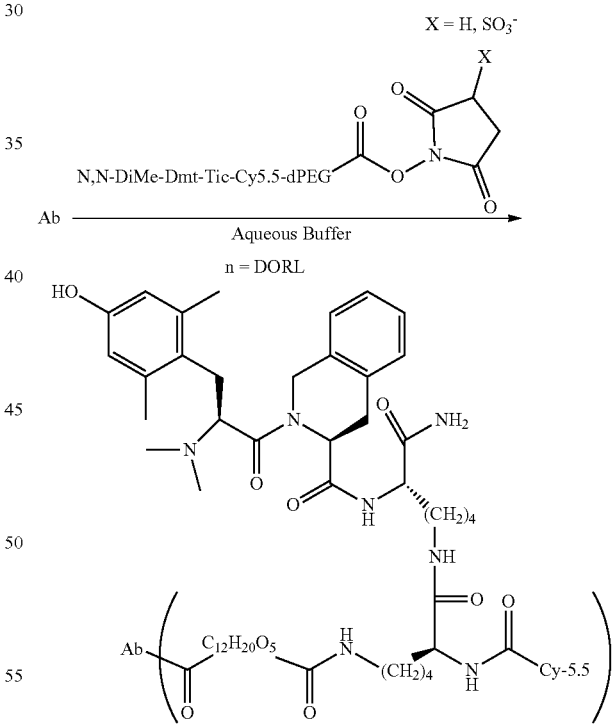

Figure 7:
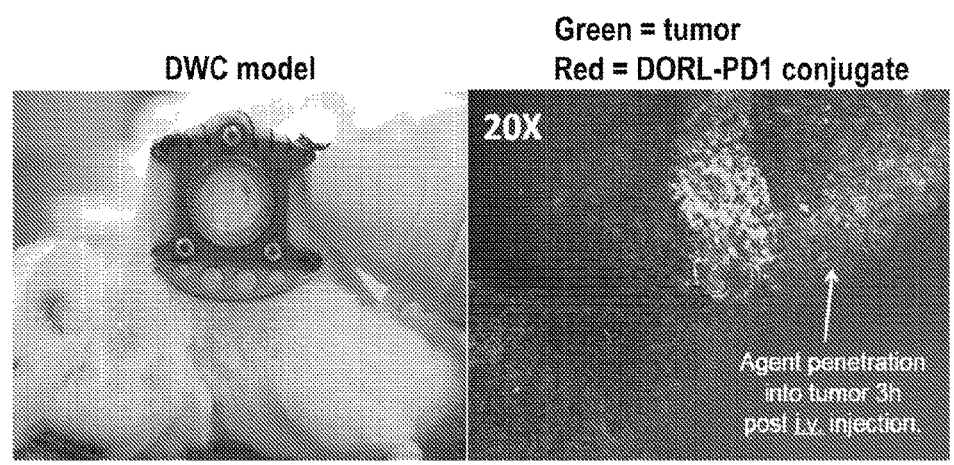
FIG. 7 shows that DORL-PD1 rapidly penetrates throughout tumor.
Figure 8:
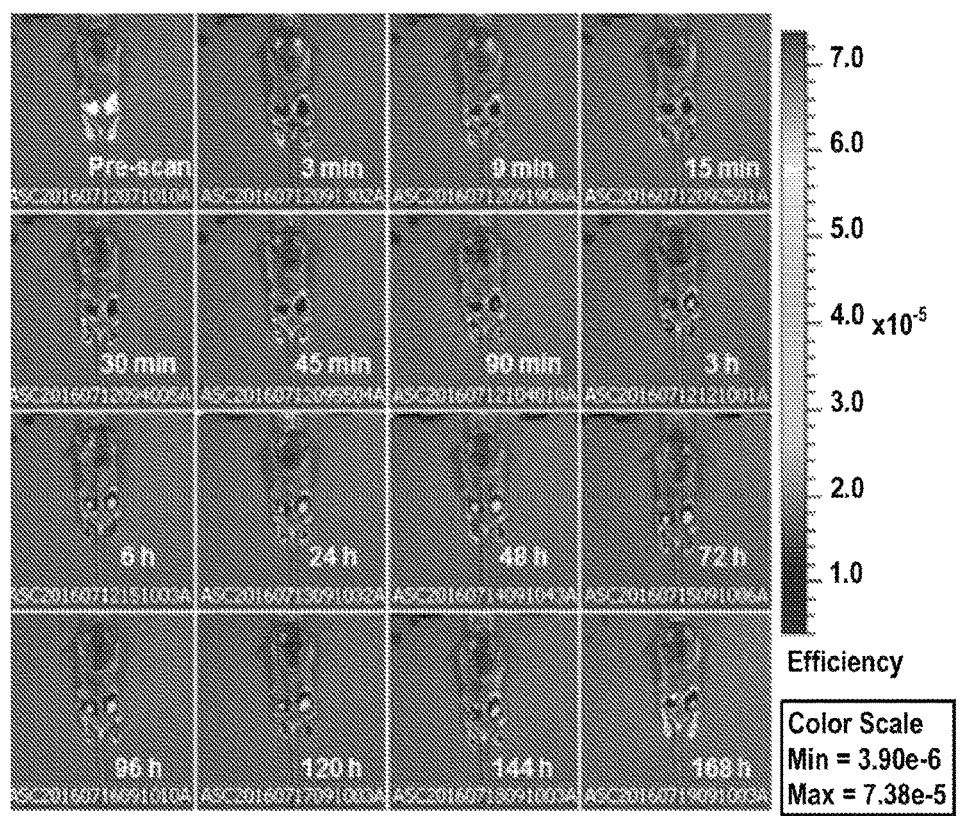
FIG. 8 shows that DORL-PD1(TAR11) is retained at higher concentrations in DOR positive tumors compared to negative and conjugates circulate for >148 h. Higher concentrations are observed in negative tumor relative to normal tissues (paw) due to EPR effect.
Figure 8:
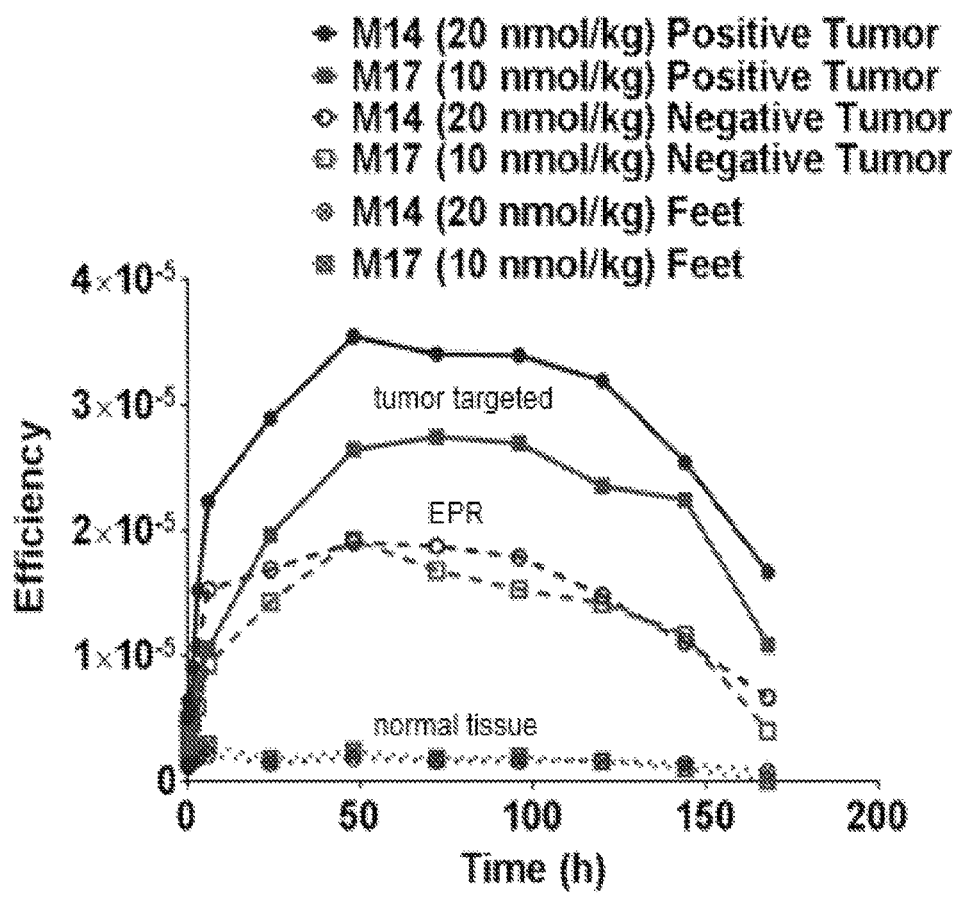
Figure 9:
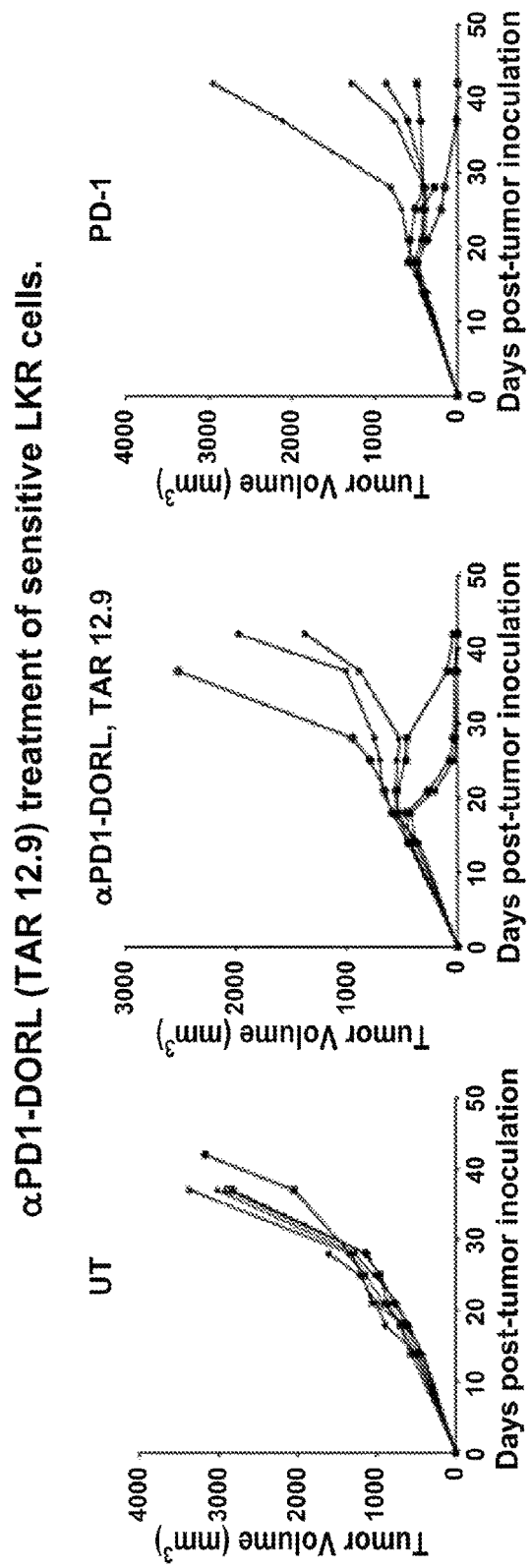
FIG. 9 shows anti PD-1 efficacy is conserved following conjugation of DORL (in sensitive LKR cells). PD-1 efficacy and αPD1-DORL efficacy in DORL-tumors is due to EPR. Targeting will decrease the dose needed for efficacy. 344 cells are refractory to anti-PD-1 therapy.
Figure 9:
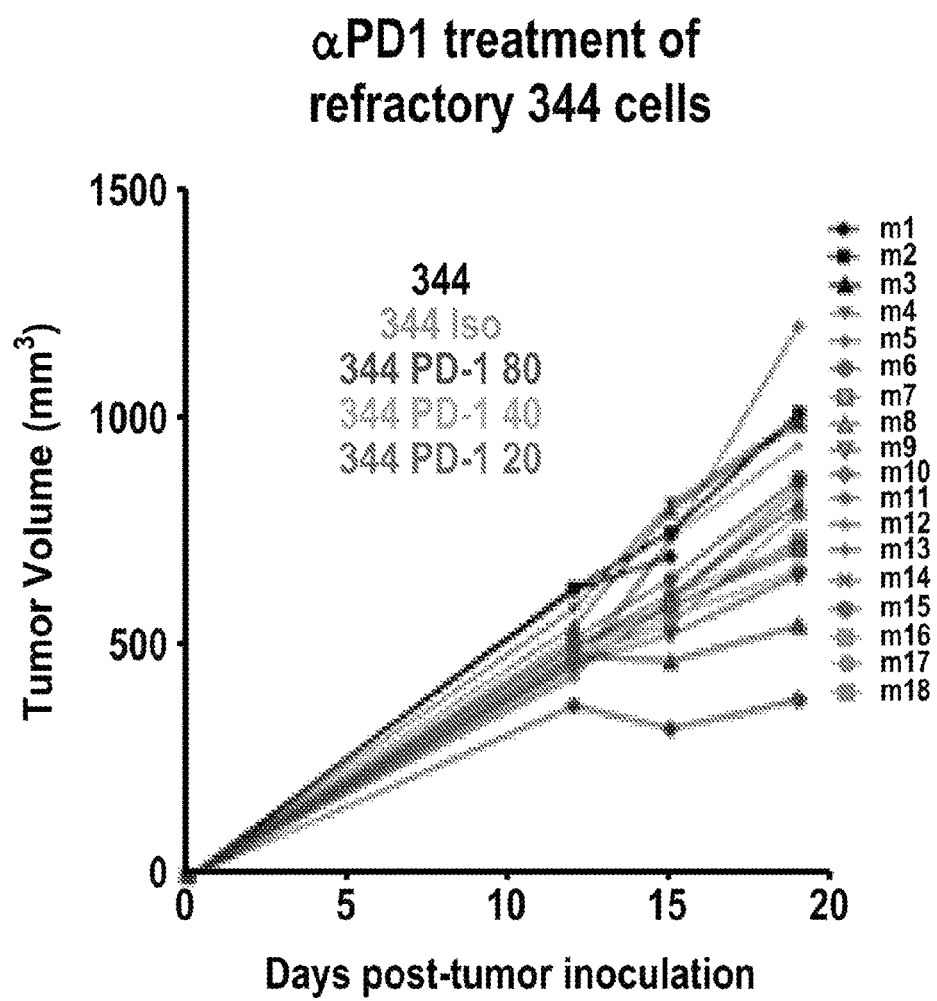

Biological Results:

DORL-PD1 rapidly penetrates throughout tumor (FIG. 7). DORL-PD1(TAR11) is retained at higher concentrations in DOR positive tumors compared to negative and conjugates circulate for >148 h. Higher concentrations are observed in negative tumor relative to normal tissues (paw) due to EPR effect (FIG. 8). Anti PD-1 efficacy is conserved following conjugation of DORL (in sensitive LKR cells). PD-1 efficacy and αPD1-DORL efficacy in DORL-tumors is due to EPR. Targeting will decrease the dose needed for efficacy. 344 cells are refractory to anti-PD-1 therapy (FIG. 9).

Figure 10:
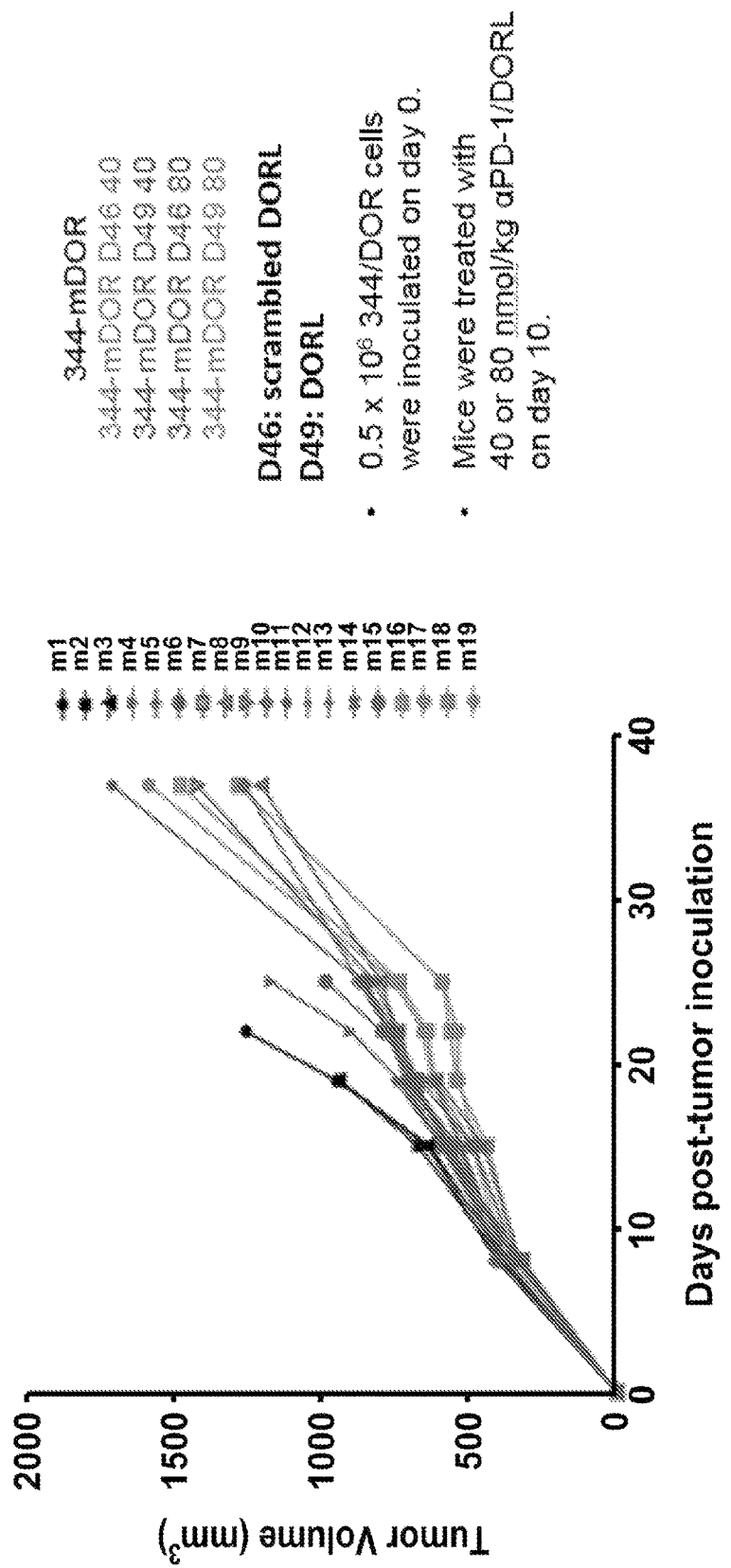
FIG. 10 shows tumor growth delay was observed in refractory 344/DOR tumors by αPD1-DORL. Delay was observed in half of clinical dose (40 nmol/kg vs. 80 nmol/kg). This delay was observed following single administration relative to the clinical 3-administration regimen.
Figure 11:
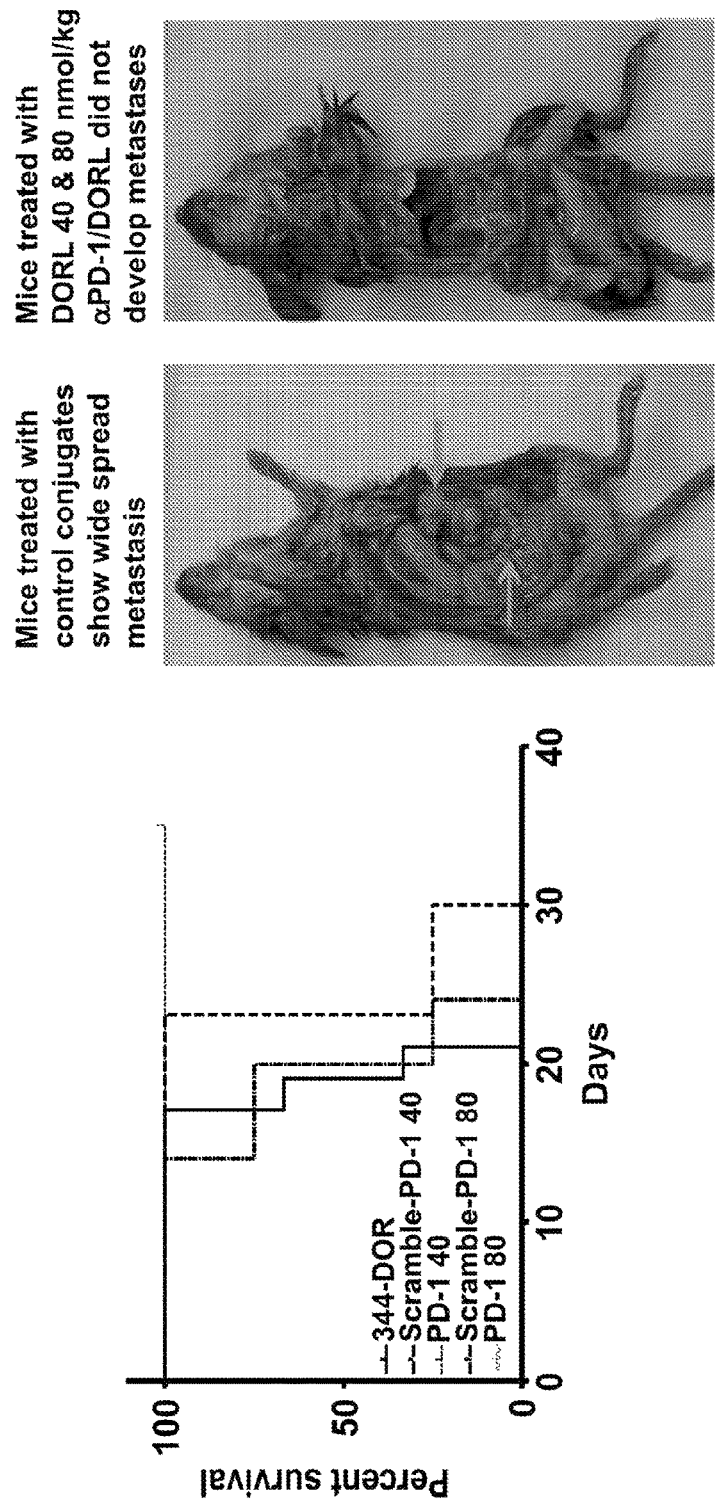
FIG. 11 shows that survival was dramatically enhanced by targeting distal metastases.

Tumor growth delay was observed in refractory 344/DOR tumors by αPD1-DORL. Delay was observed in half of clinical dose (40 nmol/kg vs. 80 nmol/kg). This delay was observed following single administration relative to the clinical 3-administration regimen (FIG. 10). Survival was dramatically enhanced by targeting distal metastases (FIG. 11).

After 3 experiments, primary tumor inhibition was not different when comparing targeted αPD1 treatment to untargeted. However, peritoneal metastasis formation was significantly decreased in targeted treatment relative to untargeted.

What is claimed is:
1. A compound having Formula I,

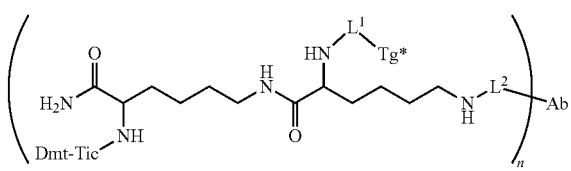

I wherein
n is an integer of from 1 to 50;
$L^1$ and $L^2$ are optional linking moieties of from 1 to 100 atoms in length; and
Ab is an antibody;
Tg* is H, a protecting group, or a detectable moiety; and
Dmt-Tic is represented by

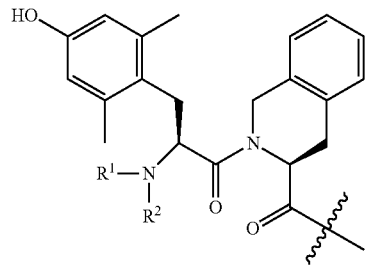

where $R^1$ and $R^2$ are independently selected from H and $CH_3$.

2. The compound of claim 1, wherein n is 4, 9, or 12.
3. The compound of claim 1, wherein Ab is specific for programed cell death protein 1 (PD1).
4. The compound of claim 1, wherein Ab is a PD-L1 antagonist, CD137 antibody, OX40 antibody, or CD40 agonist antibody.
5. The compound of claim 1, wherein the compound has the formula

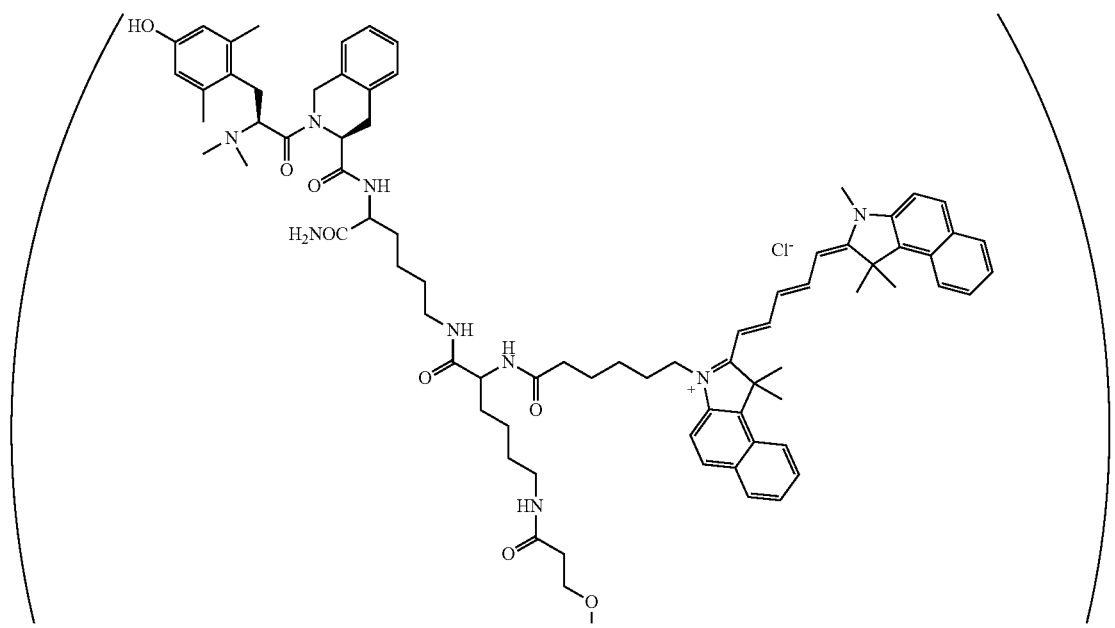

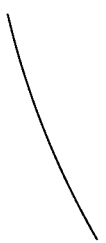  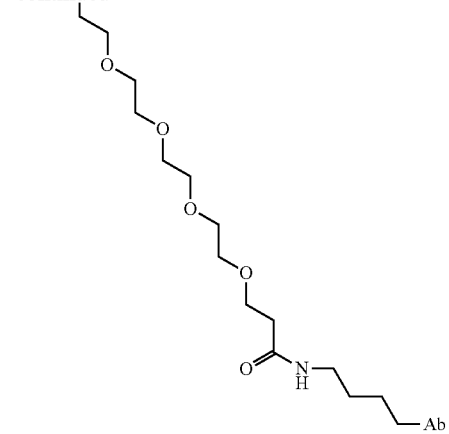

wherein Ab is an antibody and n is an integer of from 1 to 50.

6. An antibody conjugated to one or more moieties having the formula

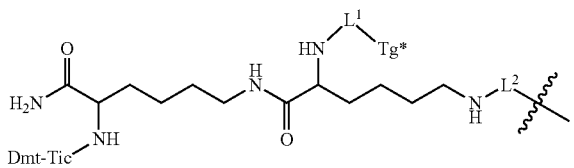

wherein
L¹ and L² are optional linking moieties of from 1 to 100 atoms in length; and
Tg* is H, a protecting group, or a detectable moiety; and
Dmt-Tic is represented by

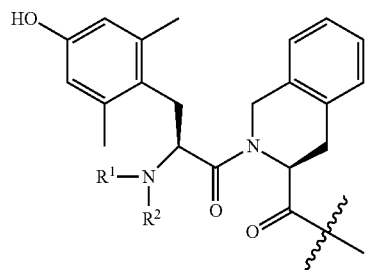

where $R^1$ and $R^2$ are independently selected from H and $CH_3$.

7. The antibody of claim 6, wherein the antibody is specific for programed cell death protein 1 (PD1), a PD-L1 antagonist, or CD137 antibody, OX40 antibody, or CD40 agonist antibody.

8. A method of treating cancers expressing delta opioid receptors, in a subject, comprising:
administering to the subject an effective amount of a composition of claim 1.

9. The method of claim 8, wherein the cancer is lung cancer.

10. The method of claim 8, wherein the lung cancer is small cell lung cancer and non-small cell lung cancer.

11. A method of decreasing peritoneal metastasis formation cancers expressing delta opioid receptors, a subject, comprising: administering to the subject an effective amount of a composition of claim 1.

12. The method of claim 11, wherein the metastasis is distal metastasis.

* * * * *